US012491380B2

(12) United States Patent
Bourhis et al.

(10) Patent No.: US 12,491,380 B2
(45) Date of Patent: Dec. 9, 2025

(54) DEVICE FOR PROVIDING A RADIATION TREATMENT

(71) Applicants: CENTRE HOSPITALIER UNIVERSI-TAIRE VAUDOIS (C.H.U.V.), Lausanne (CH); CERN—EUROPEAN ORGANIZATION FOR NUCLEAR RESEARCH, Geneva (CH)

(72) Inventors: Jean François Marie Bourhis, Lausanne (CH); Jean-François Germond, Chez-le-Bart (CH); Raphaël Moeckli, Echichens (CH); Walter Wuensch, Onex (CH); Alexander Gerbershagen, Meyrin (CH)

(73) Assignees: Centre Hospitalier Universi-Taire Vaudois (C.H.U.V.), Lausanne (CH); CERN—European Organization For Nuclear Research, Geneva (CH)

( * ) Notice: Subject to any disclaimer, the term of this patent is extended or adjusted under 35 U.S.C. 154(b) by 448 days.

(21) Appl. No.: 18/002,601

(22) PCT Filed: Jun. 23, 2021

(86) PCT No.: PCT/EP2021/067189
§ 371 (c)(1),
(2) Date: Dec. 20, 2022

(87) PCT Pub. No.: WO2021/260028
PCT Pub. Date: Dec. 30, 2021

(65) Prior Publication Data

US 2023/0226378 A1 Jul. 20, 2023

(30) Foreign Application Priority Data

Jun. 24, 2020 (EP) .................................... 20181826

(51) Int. Cl.
*A61N 5/10* (2006.01)
*H05H 7/02* (2006.01)
*H05H 7/12* (2006.01)
*H05H 9/00* (2006.01)

(52) U.S. Cl.
CPC ............. *A61N 5/1078* (2013.01); *H05H 7/02* (2013.01); *H05H 7/12* (2013.01); *H05H 9/00* (2013.01);
(Continued)

(58) Field of Classification Search
CPC ......... A61N 5/1078; A61N 2005/1089; H05H 7/02; H05H 7/12; H05H 9/00; H05H 2007/022; H05H 2007/025; H05H 2277/11
See application file for complete search history.

(56) References Cited

U.S. PATENT DOCUMENTS

2013/0231516 A1 9/2013 Loo et al.
2014/0270086 A1* 9/2014 Krasnykh ................ H05G 2/00 378/124

(Continued)

FOREIGN PATENT DOCUMENTS

WO WO2015/038832 A1 3/2015
WO WO2021058624 A1 4/2021

OTHER PUBLICATIONS

Maxim, P. et al., PHASER: A platform for clinical translation of FLASH cancer radiotherapy, Radiotherapy and Oncology, 139: 28-33, 2019.

*Primary Examiner* — Nicole M Ippolito
(74) *Attorney, Agent, or Firm* — Weston R. Gould; Dinsmore & Shohl LLP

(57) ABSTRACT

The present relates to a device for providing a radiation treatment to a patient comprising: —an electron source for providing a beam of electrons, and —a linear accelerator for
(Continued)

accelerating said beam until a predetermined energy, and —a beam delivery module for delivering the accelerated beam from said linear accelerator toward the patient to treat a target volume with a radiation dose, The device further comprises intensity modulation means configured to modulate the distribution of the radiation dose in the target volume according to a predetermined pattern. The pattern is determined to match the dimensions of a target volume of at least about 50 $cm^3$, and/or a target volume located at least about 5 cm deep in the tissue of the patient with said radiation dose, The radiation dose distributed is up to about 20 Gy delivered during an overall treatment time less than about 50 ms.

17 Claims, 4 Drawing Sheets

(52) U.S. Cl.
CPC ................ *A61N 2005/1089* (2013.01); *H05H 2007/022* (2013.01); *H05H 2007/025* (2013.01); *H05H 2277/11* (2013.01)

(56) References Cited

U.S. PATENT DOCUMENTS

| | | | | |
|---|---|---|---|---|
| 2014/0376697 | A1* | 12/2014 | Barty | H05G 2/00 378/119 |
| 2019/0022422 | A1 | 1/2019 | Trail et al. | |
| 2022/0387824 | A1* | 12/2022 | Bourhis | A61N 5/1077 |

* cited by examiner

DEVICE FOR PROVIDING A RADIATION TREATMENT

CROSS REFERENCE TO RELATED APPLICATIONS

This application is a U.S. National Stage under 35 U.S.C. § 371 of PCT/EP2021/067189 filed Jun. 23, 2021, which depends from and claims priority to European application number 20181826.7 filed Jun. 24, 2020, the entire contents of each of which are incorporated herein by reference.

TECHNICAL FIELD

The present invention relates to a device for radiation treatment comprising intensity modulation means, in particular a device for ultra-short time intensity modulated radiation treatment.

BACKGROUND OF THE ART

Cancer is a dominant worldwide cause of death, mainly treated by surgery, radiotherapy (RT) and chemotherapy. There is a rapid increase of its incidence but only a slow improvement in curability, despite recent progress notably in immunotherapy, robotics surgery, and the introduction of new molecular targeted drugs.

Since the pioneered work of Roentgen and Marie Curie in the early 20$^{th}$ century, radiotherapy remains an essential tool for treating cancer. Although recent development in radiotherapy allowed these treatments to be more precise and more effective, the remaining side effects are still a problem that limits its use, for instance damages to healthy tissue.

Delivering high curative radiation doses to tumors depends on the ability to spare normal tissues from harmful effects of radiation. Over the last decades precise dose distribution optimization over target volume and healthy tissues appeared as the most powerful tool to obtain a differential effect between normal tissues and tumors thereby minimizing the side effects.

One of the most efficient tool for achieving high conformality is intensity modulated radiotherapy (IMRT) which is using multiple converging beams, each of them delivering a small part of the dose which is resulting in a highly conformal distribution of the total dose. In conventional radiotherapy, IMRT is planned with a specific inverse treatment planning system and delivered via a rotation of the irradiation source along with mechanical modulation of the beam through multileaf collimators. For proton treatments, intensity modulation of the beam is obtained with a fixed proton source and magnetic scanning, allowing to achieve optimal proton conformality (Intensity Modulated Proton therapy, IMPT)

A complementary emerging solution to limit radiation-induced damage on normal tissue is to reduce the irradiation time in so called FLASH Radiotherapy (RT) or FLASH Therapy. A conventional radiotherapy treatment generally aims at administering a total dose of 20 to 70 Gy to each tumor, typically in doses of 2 Gy per fraction, each fraction being administered over several minutes. During the past few years, a number of experiments have been carried out which demonstrate that RT with ultra-short irradiation times (below 50 ms) can significantly reduce the side effects.

FLASH radiotherapy is a biological phenomenon showing that ultra-high dose rate can induce a remarkable sparing of normal tissues, while the effect on tumors is preserved intact, when compared to identical radiation dose with conventional dose rate, and resulting in a more effective treatment. Published experiments have reported that this biological FLASH effect can be obtained under specific conditions when using a few ultra-intense pulses with a ultra-high dose rate in the pulse (typically a dose per pulse above 1.5 Gy and mean dose rate above $10^6$ Gy within pulse), and when a high total dose of radiation (>10-20 Gy) is given in an overall duration in the range of milliseconds (ms), for example delivering 20 Gy should be done in at least less than 50 ms.

During the ultra-short time scale of FLASH delivery, it is not known how to use intensity modulation of the dose within each beam, in order to provide highly conformal dose distribution in FLASH treatments. The use of mechanical modulation with multi leaf collimators is not feasible in the FLASH time scale.

In clinical situations of tumor deep in the body, obtaining high conformality with IMRT requires multiples beams, typically up to one hundred beams, all converging into the target, whereas using multiple beams is not compatible with a FLASH effect, since a biological FLASH sparing of normal tissues was essentially observed when using high single dose, typically at least between 10 and 30 Gy per beam.

Therefore, when it comes to provide highly conformal dose distribution for deep seated tumor and/or large tumor in a FLASH treatment, the existing solutions are not capable of meeting the FLASH requirements.

SUMMARY OF THE INVENTION

The above problems are solved, or at least partially solved, by the device and the method according to present invention.

The invention concerns a device for providing a radiation treatment to a patient, the device comprising:

- an electron source for providing a beam of electrons, and
- a linear accelerator for accelerating said beam until a predetermined energy, and
- a beam delivery module for delivering the accelerated beam from said linear accelerator toward the patient to treat a target volume with a radiation dose, characterized in that the device further comprises intensity modulation means configured to modulate the distribution of the radiation dose in the target volume according to a predetermined pattern matching the target volume, the pattern comprising several subsections and each subsection corresponds to a portion of the target volume so that the intensity modulation means allow to set the radiation dose received by each portion of the target volume, the pattern is determined to match the dimensions of a target volume of at least about 50 cm$^3$, and/or a target volume located at least about 5 cm deep in the tissue of the patient with said radiation dose, the device being further characterized in that the radiation dose distributed by said intensity modulation means is up to about 20 Gy, the radiation dose being delivered during an overall treatment time less than about 50 ms.

The dimensions of the target volume is preferably at least about 100 cm3, more preferably at least about 250 cm3, more preferably at least about 500 cm3, more preferably at least about 750 cm3, more preferably at least about 1000 cm3, more preferably at least about 2000 cm3, more preferably at least about 3000 cm3.

The target volume is located at least about 5 cm deep in the tissue of the patient, meaning that the whole target volume is at least 5 cm deep in the tissue of the patient.

Preferably, the target volume is at least about 10 cm deep in the tissue of the patient, at least about 15 cm, at least about 20 cm, at least about 25 cm.

The radiation dose is preferably up to about 30 Gy, more preferably up to about 40 Gy.

Preferably, the overall treatment (i.e. radiation treatment) time is less than about 10 ms, more preferably less than about 1 ms.

The present invention concerns a device for ultra-short time intensity modulated radiation treatment to trigger a FLASH effect for delivering an intensity modulated radiation dose.

In the present invention the radiation dose, i.e. the entire radiation dose, is delivered in a time scale where FLASH effect has been observed, for instance typically for a dose of 20 Gy in less than 50 ms.

Intensity modulation describes a technique in which the dose is made to be dependent on position inside the target volume. The present invention allows to use intensity modulation means for electron therapy on FLASH time scale (i.e overall treatment time below 50 ms). The clinical purpose of intensity modulation is essentially to achieve optimal conformality for optimal coverage of the target volume.

The claimed solution is addressing the combination of FLASH treatment and dose intensity modulation with the aim of providing highly conformal FLASH therapy (=intensity modulated FLASH therapy).

Combining both FLASH conditions and intensity modulation of the dose is providing two powerful complementary tools for sparing normal tissues, while delivering optimal high curative dose in the tumors. This combination will markedly enlarge the potential applications of radiotherapy for cancer treatments.

The device of the present invention comprises intensity modulation means configured to modulate the distribution of the radiation dose in the target volume. The target volume is irradiated according to a pattern of sub-sections, each subsection corresponding to a portion of the target volume.

Intensity modulation requires that portions, corresponding to subsections of the pattern, of the target volume be irradiated independently and that the dose in each subsection of the pattern be controlled independently so that each subsection can have its own intensity and energy. In other words, the pattern is a map and each subsection of the pattern correspond to coordinates of a portion of the target volume. Advantageously, the pattern comprises shifted bunch trains modulated in charge and energy.

Preferably, in the plane transverse to the beam, subsections are formed by focusing the beam to a size smaller than target volume cross section.

The focusing can be adjusted from irradiating the entire target cross section down to the preferred value of 1/10 of the target cross section per beam, preferably 1/100.

The subsection's shape can be adjusted from circles to elongated ellipses and into arbitrary shapes, like rectangles or hexagons.

In the state of the art of clinical radiotherapy, intensity modulation refers either to

- changing during radiation the position of the leaves of a multi-leaves collimator (VMAT or step & shoot) and the pulse repetition rate or
- continuous scanning pencil beams of constant dose (PBS, pencil beam scanning for protons for instance).

Therefore, in the above mentioned methods from the state of the art, the total intensity of the combined field is modulated, not directly the features (charge, energy of instance) of each train of particles. This is completely different in the present invention. In the present invention, the intensity modulation means are modulating the charge and energy of the bunch trains individually in order to produce an intensity modulated total field.

The intensity modulation means of the present invention allow the radiation dose to be controlled in the tumor cross section (independently for each incoming beam line in case of multiple beam lines) by adjusting the position, total charge and energy of each electrons bunch within a train and between trains of electrons bunches.

The pattern is determined to match the dimensions of a target volume, for instance of at least about 50 $cm^3$, and/or a target volume located at least about 5 cm deep in the tissue of the patient with said radiation dose. In other words, the present invention is capable of delivering an intensity modulated radiation dose of at least 20 Gy to large target volume (meaning for instance at least 50 cm3) or deep seated target volume (for instance at least 5 cm deep) in ultra short overall time (meaning below 50 ms) whereas the existing radiotherapy devices fail to achieve all these requirements simultaneously.

In the present invention, the key parameters to provide an intensity modulated radiation dose under FLASH conditions, namely a radiation dose of at least 20 Gy to large target volume or deep seated target volume in ultra short overall time (meaning below 50 ms) are achieved at the same time, concurrently.

In a preferred embodiment, the pattern corresponds to a treatment plan that can be selectively chosen from homogeneous to a specified heterogeneous radiation dose distribution, depending on the clinical specifications of each individual patient.

The pattern preferably corresponds to a gradient of dose intensity to distribute the radiation dose gradually in the target volume. The pattern is advantageously chosen using a treatment planning system dedicated for FLASH treatments.

The pattern advantageously depends on (one or a combination of the following factors):

- the dimension and/or the shape of the target volume;
- the proximity of critical organs and/or healthy tissues;
- the number and orientation of the radiation beams;
- the radiation dose required in each subsection;

The accelerated beam comprises several trains of particles bunches. Each train and each bunch within a train has a total charge and energy that can be set. The dose from each bunch train is determined by the charge of each bunch train. The charge per bunch train can be specified by the number of bunches in a bunch train and the charge per bunch. Bunch number setting is the preferred means of specifying bunch train charge and gives a charge range, and thus dose range.

The intensity of a train is given by the charge per bunch and the number of bunches per train, which gives the dose that is provided by each train to a portion of the target volume. The intensity modulation means according to the present invention allow to set the charge of each train independently and to direct each train to a predetermined position which modulates the distribution of dose in the target volume.

Two trains of electrons bunches can have the same charge and be directed to a different portion or to the same portion of the target volume. Alternatively, two trains of electrons bunches can have a different charge and be directed to a different portion or to the same portion of the target volume.

In another example, the charge can vary for each train while its energy is kept fixed. In this example, a 100 MeV train can have a charge of 100 nC or 300 nC which gives a correspondingly different dose. By distributing the 100 nC or 300 nC trains in separate subsections, it is possible to achieve intensity modulation, in particular transverse to the direction of the beam.

The intensity can also be modulated by varying both the energy of each train and the energy of each bunch within the train. In another example, there are a 100 MeV train and a 102 MeV train in the accelerated beam, the 100 MeV having a charge of 300 nC and the 102 MeV having a charge of 100 nC. By setting the train's energy, it is possible to achieve intensity modulation transverse to the direction of the beam as well as longitudinal to the direction of the beam, since different energy beams follow different trajectories in the beam lines and the higher is the energy, the deeper the train goes. Varying the energy of the train within a beam line has two effects: 1) the train arrives at the patient in different positions (transverse modulation), 2) the beam penetration changes (longitudinal modulation).

In one embodiment each portion receives a radiation dose up to the entire radiation dose, said radiation dose being for instance at least about 20 Gy. The entire radiation dose is delivered in less than 50 ms. Thus, for instance when the entire radiation dose is 20 Gy and the pattern comprises ten subsections, each subsection can receive a dose up to 20 Gy. The entire dose, also named the prescribed dose, is the total dose the target volume shall receive in less than 50 ms, preferably in a single session of less than 50 ms.

The entire dose can be increased to at least 35 Gy, preferably of at least 40 Gy, preferably in less than 50 ms.

In an embodiment, each portion receives at least one train of electrons bunches. The train of electrons has a specific total charge and energy. This gives the means to profile the dose in the tumor in three dimensions providing high conformality for the whole radiation treatment.

In a preferred embodiment, the electron source is a very high energy electron beam with a charge of at least about 1000 nC, preferably at least about 1500 nC.

The electron source is preferably stationary (for instance relative to the patient). It means that during the radiation treatment, the electron source is preferably immobile, i.e. motionless or not moving.

In an embodiment, the electron source is arranged for example for delivering up to twenty trains of electrons bunches of at least 150 nC each in said overall time. The bunch charge is adjustable with nominal around 0.5 nC and a train is 300 bunches.

In an embodiment, the accelerated beam is composed of a plurality of trains of electrons bunches, the intensity modulation means are configured to modulate the radiation dose by separating the trains of electrons bunches depending on the charge and/or energy of each train. Each subsection of the pattern corresponds to a portion of the target volume that is irradiated independently with at least one train of electrons bunches having a determined energy and total charge.

In one embodiment, the intensity modulation means comprises charge variation means to set the charge of each train independently and direct each train to a predetermined subsection of the pattern to reach a corresponding portion of the target volume which modulates the distribution of radiation dose in the target volume.

For instance, the intensity modulation means comprise deflecting means for deflecting each train of electrons bunches position transversely relative to the accelerated beam direction, said deflecting means having a deflecting speed faster than the interspacing time between two subsequent trains.

The deflecting means are in one embodiment electromechanical means.

In another embodiment, the deflecting means are electromagnetic means such as magnet or deflecting magnet, for instance dipole magnets or quadrupole magnets with time varying magnetic fields, or dipole coils. The magnets of the intensity modulation means are for instance fast ramping magnets or magnets capable of fast field-ramping.

In another embodiment the deflecting means is a radio frequency deflector. Such a deflector can impose a time-varying a transverse momentum on the different bunches within a train resulting in complex bunch position patterns at the target—by which the intensity is modulated. The transverse momentum is varied by giving an amplitude and phase variation to the radio frequency pulse that powers the deflector. A radio frequency deflector is typically placed at the end of the linear accelerator (linac).

Each deflecting magnet can deflected along two orthogonal axes, for instance by two orthogonal pairs of dipole coils. A specific setting of the magnetic field gives a specific beam trajectory and thus arrival position in the target cross section.

In order to direct the successive bunch trains to the specified positions of each subsection, the magnetic field of the deflecting magnet is set in a specific sequence of values at the times of passage of the successive bunch trains, thus giving a specific sequence of beam trajectories. This is done by adjusting the current in the magnet in the time between the bunch train passages. This means that the entire deflection is completed (in all beam lines in case of multiple beam lines) within the specified overall treatment time of less than 50 ms, preferably less than 10, more preferably less than 1 ms. The bunch trains follow the specified trajectories and sequentially irradiate the specified portions of the target volume.

The deflecting means may be at the end of the linear accelerator (or in the beam delivery lines in case of multiple beam lines). The preferred solution is one deflecting magnet at the end of each beam line. The deflecting means are preferably capable of deflecting each train of electrons bunches transversely to optimally cover the target volume.

For instance, the deflecting means are implemented in the linear accelerator or in the delivery module.

In one embodiment, the intensity modulation means comprises energy variation means to set the energy of each train or of each bunch within the train independently and direct each train or each bunch (if the energy of each bunch is set) to a predetermined subsection of the pattern to reach a corresponding portion of the target volume which modulates the distribution of radiation dose along the direction of the accelerated beam through the target volume. Specifically the longitudinal distribution of dose depends on energy, so that the greater the energy, the deeper it goes into the target volume (into the tissues). Therefore, modulating the energy of the trains of electrons bunches allows to modulate the intensity along the direction of the accelerated beam (or along each beam lines in case of multiple beam lines). By irradiating the target volume with trains of electrons bunches of specified energy, a longitudinal (in the direction of the beam) intensity modulation is produced.

In one embodiment, the energy variation means are set for implementing predetermined energy variations between each train of electrons bunches, said energy variation means being preferably operated from the linear accelerator. Preferably, each train has an energy which differs from about 1% to about 5%. In case of multiple beam lines, the energy range between trains within a beam line is restricted to be less than the beam line selection energy difference.

For instance the energy variation means are operated by controlling the amplitude and the phase of the radiofrequency pulses of the linear accelerator. The energy of each train of electrons bunches at the end of the linear accelerator is determined by the amplitude of the radio frequency fields in the linear accelerator and by the relative phase between the beam and the radio frequency pulse.

The energy of the bunches within a train, and entire bunch trains, can be varied through radio frequency pulse specification, through programmed amplitude and phase of the radio frequency pulse feeding the accelerating structures. Thus beam energy can be used for both inter and intra-bunch train positioning. Preferably, variation in energy of each train and within each train of bunches is used concomitantly to profile the specified dose distribution both in transverse and in the longitudinal axis, within the FLASH time scale (less than 50 ms).

Increasing energy modulation means may be clinically interesting since an energy variation has the potential to provide an additional degree of freedom along the direction of the accelerated beam that could contribute for obtaining optimal dose distribution (the higher is the energy within each subsection, the deeper this subsection beam is delivering the dose).

The charge variation means is accomplished preferably by changing the number of bunches per train and/or by changing the charge per bunch.

In one embodiment, the accelerated electron beam is separated into a plurality of beam lines by separating means, preferably two or three beam lines, each beam lines being separated by a determined angle, and subsequently focusing each of said beam lines toward the patient to arrive in an overall time of less than 50 ms, preferably less than 10 ms, and more preferably less than 1 ms, on the target volume, each beam line further comprising independent intensity modulation means.

For instance, the separating means are chosen among the list comprising energy-based separating means by using magnetic spectrometer, radio frequency deflector based means.

Preferably, each beam line has an energy with differs from about 10% to about 40%. In case of multiple beam lines, the beam line selection energy difference is greater than the energy range between trains within a beam line.

Advantageously, each of the beam lines is equipped with an independent intensity modulation means. This allows an independent intensity modulation for each beam to obtain the needed optimal conformality of the delivered dose to the target volume.

Preferably, the target volume is irradiated from two or three beam lines with independent intensity modulation in each beam line. In a preferred embodiment, the intensity modulation means comprise a combination of charge variation means, energy variation means, deflection means, and multiple beam lines. This combination allows an intensity modulation in three dimensions. The optimal intensity modulation is preferably specified depending on the target volume definition and nearby organs at risk.

In one embodiment, the accelerated electron beam having a predetermined energy between about 30 MeV and about 250 MeV, preferably between about 50 MeV and about 250 MeV, more preferably between about 50 MeV and about 150 MeV.

The present invention further relates to a method for treating a tumor target volume of a patient, the method comprising:

Providing a device according to the invention;

Determining a target volume of at least about 50 $cm^3$, and/or a target volume located at least about 5 cm deep in the tissue of the patient with said radiation dose, Determining a pattern matching the target volume dimensions, the pattern comprising several subsections and each subsection corresponds to a portion of the target volume so that the intensity modulation means allow to set the radiation dose received by each portion of the target volume, Configuring the intensity modulation means of the device to modulate the distribution of the radiation dose in the portions of the target volume according to the predetermined pattern;

Delivering the radiation dose to the target volume according to the predetermined pattern, said radiation dose distributed by said intensity modulation means being up to about 20 Gy preferably at least up to about 30 Gy, more preferably at least up to about 40 Gy, during an overall treatment time less than about 50 ms, preferably less than about 10 ms, more preferably less than about 1 ms.

The present invention allows to provide a high radiation dose (i.e. at least 20 Gy) with a highly conformal modulated intensity delivered in FLASH conditions (i.e. less than 50 ms).

The particular advantages of the method are similar to the ones of the device of the invention described herein and will thus not be repeated here.

An optimal dose distribution is obtained due to the unique combination of high conformality and FLASH conditions. The treatment according to the present invention can be used to treat all types of tumors.

Advantageously, intensity modulated FLASH therapy uses high dose per fraction with a high index of conformality, a very small number of fractions for a treatment is expected for each patient to deliver the entire radiation dose, for instance between 1 to 3 fractions, preferably 1 or 2 fractions In one embodiment, the method further comprises:

Setting the intensity modulation means to modulate the radiation dose by separating the trains of electrons bunches depending on the charge and/or energy of each train;

In one embodiment, the method comprises:

Setting the charge of each train independently and direct each train to a predetermined subsection of the pattern to reach a corresponding portion of the target volume which modulates the distribution of radiation dose in the target volume;

In one embodiment, the method comprises:

Setting the energy of each train independently and direct each train to a predetermined subsection of the pattern to reach a corresponding portion of the target volume which modulates the distribution of radiation dose along the direction of the accelerated beam through the target volume.

In one embodiment, the method comprises:

Separating the accelerated electron beam into a plurality of beam lines by separating means, preferably two or three beam lines, each beam lines being separated by a determined angle, and subsequently focusing each of said beam lines toward the patient to arrive in an overall time of less than 50 ms, preferably less than 10 ms, and more preferably less than 1 ms, on the target volume, each beam line further comprising independent intensity modulation means.

Preferably, the pattern comprises between 5 and 10 subsections per beam, each of them with a high dose intensity.

In a preferred embodiment, the treatment comprises:

Administrating at least one train of electrons bunches per subsection, preferably one or two trains of electrons bunches per subsection, each dose per subsection being modulated up to about 20 Gy per subsection, preferably up to 30 Gy per subsection, more preferably up to 40 Gy per subsection, In the present invention, ultra-high dose rate radiation treatment or ultra high dose rate high dose irradiation means FLASH radiotherapy or FLASH Therapy. FLASH radiotherapy can be defined as a radiotherapy treatment which spares healthy tissues as compared to conventional RT dose rate, while preserving intact the effect on tumors.

As used herein, the terms "ultra-high dose rate radiation dose" means the total dose delivered to the patient target volume.

As used herein, the term "about" applies to numeric values or ranges of numeric values and refers to a range of numbers that one of skill in the art would consider equivalent to the recited values, i.e. plus or minus ten percent. For example, "about 10 cm" refers to 10 cm+/−10%, i.e. 9.9 cm to 10.1 cm. In the present invention, a dose refers to the radiation dose in Gy delivered to the patient. A dose can be administered in several fractions.

As used herein the term "patient" is well-recognized in the art, and refers to a mammal, including dog, cat, rat, mouse, monkey, cow, horse, goat, sheep, pig, camel, and, most preferably, a human. In some embodiments, the patient is a patient in need of treatment or a patient suffering from cancer. However, in other aspects, the patient can be a normal subject. The term does not denote a particular age or sex. Thus, adult and newborn patients, whether male or female, are intended to be covered.

As used herein the terms "at least up to X" means a value superior to zero and up to X.

As used herein, the term "radio wave pulse" refers to the pulse of radio wave used in the linear accelerator. The linear accelerator uses radio wave pulses of microwave power to accelerate a radiation beam from a radiation source, for instance an electron beam from an electron source. For instance, these radio wave pulses are around 250 ns long and can be repeated with repetition rate of 1 kHz, that is with a period of 1 ms, in burst mode. For example, the frequency of the microwaves is X-band, specifically 12 GHz, but can also be C (5.7 GHz) or S (3 GHz) band.

As used herein, the terms "radiation pulse" refer to the pulse of particles after the linear accelerator. Each pulse accelerates at least a train of particles bunches, for instance electron bunches if the radiation beam is an electron beam. For example, the particles bunches are about 1 ps long and come every 1 ns, so that there are 250 particles bunches in a 250 ns radio wave pulse. Each particles bunch has a charge of 1 nC giving a total charge of 2500 nC (before collimation) and an average current during the pulse of 1 A.

As used herein, the word "means" (singular or plural) preceded or followed by a function can be replaced by the word "unit" or "module". For instance "intensity modulation means" can be replaced by "intensity modulation unit" or "intensity modulation module".

In the present invention, the accelerated beam is composed by a plurality of trains, each train comprises a plurality of bunches, each bunch is made of a plurality of particles. For example, in a treatment there are 20 trains, each train comprises 300 bunches and each bunch has a charge of 1 nC (one nanoCoulomb, which corresponds to $6.2\times10^9$ electrons). Regarding the times, for example, smallest to largest, each bunch is approximately 1 ps long (0.3 mm at the speed of light) and there is 1 ns between bunches. In this example, with 300 bunches/train, a train is thus 300 ns long and 20 trains when delivered every 2.5 ms arrive at the patient over a treatment time of 50 ms.

The embodiments describe herein for the device also apply to the methods according to the present invention mutatis mutandis.

The present invention can comprise one embodiment or a combination of embodiments.

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

The present detailed description is intended to illustrate the invention in a non-limitative manner since any feature of an embodiment may be combined with any other feature of a different embodiment in an advantageous manner.

Figure 1:
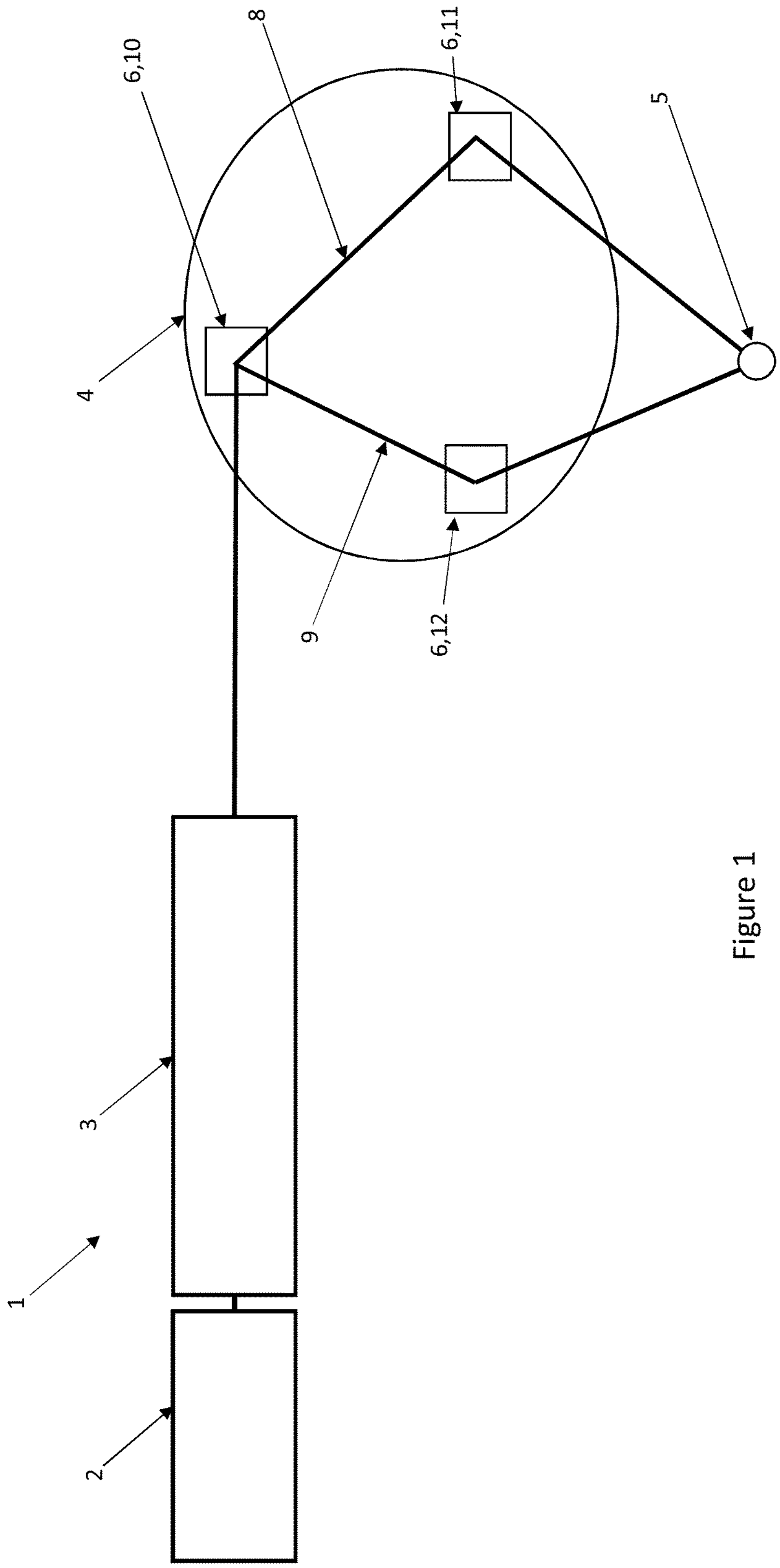
FIGS. 1 and 2 represent a first embodiment of the device according to the present invention, FIG. 1 being a general overview and FIG. 2 a detailed view of the beam delivery module of the device.
Figure 2:
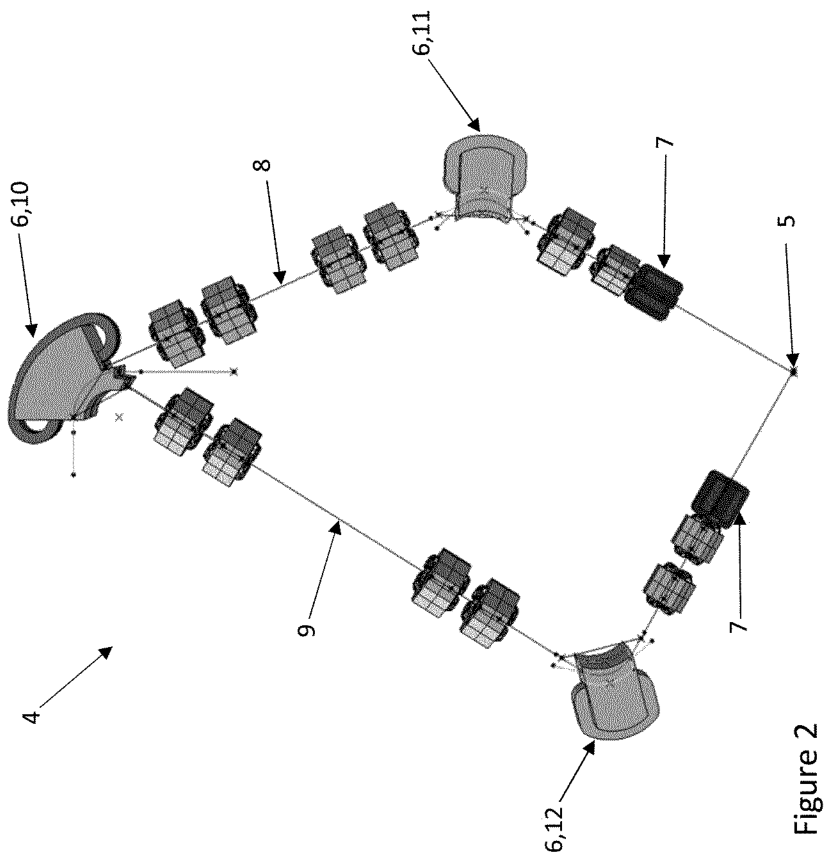

FIGS. 1 and 2 represent a device 1 according to the present invention according to a first embodiment, FIG. 1 being a general overview and FIG. 2 a detailed view of the beam delivery module of the device.

The device 1 comprises an electron source 2, a linear accelerator 3 and a beam delivery module 4. The device 1 is arranged for delivering a radiation dose to a target volume 5 of a patient.

The radiation source 2 is a high current electron source, in particular a Radiofrequency laser-driven photo-injector.

The linear accelerator 3 is a high current X-Band linac. The linac has parameters of eight half meter long accelerating structures, operating with a beam-loaded gradient of 35 MV/m. The linac is powered by two 50 MW peak power X-band klystrons and radiofrequency pulse compressors. FIG. 2 is a detailed view of the beam delivery module 4. The role of the beam delivery module 4 is to guide the beam from the electron source 2 until the target volume 5 of the patient. The beam delivering module 4 comprises separating means 6 and intensity modulation means 7.

The accelerated beam is first split into two distinct beam lines 8,9 by separating means 6, i.e. a high momentum beam line 8 and a low momentum beam line 9.

In this example, the separating means 6 is a splitter dipole 10 (separator magnet) to separate the accelerated beam exiting the linear accelerator 3 into two distinct beam lines. The splitter dipole 10 has with the following parameters:

Size: 1000 mm×850 mm×800 mm

Weight: 3000 kg

Material: iron yoke, copper coils

Bending angle: 122 degrees (for low momentum beam); 65.5 degrees (for high momentum beam)

Central field: 1.0 T

Effective length: 0.555 m (for low momentum beam); 0.665 m (for high momentum beam)

Then, the separating means 6 further comprises one dipole 11,12 on each beam line 5,6, i.e. a dipole of high momentum 11 on the high momentum beam line 6 and a dipole of low momentum 12 on the low momentum beam line 9.

The dipole of high momentum 11 has the following parameters:

Size: 700 mm×735 mm×450 mm
Weight: 1500 kg
Material: iron yoke, copper coils
Bending angle: 54.5 degrees
Central field: 0.95 T
Effective length: 0.5 m
Current: 22.4 A The dipole of low momentum 12 has the following parameters:

Size: 700 mm×735 mm×450 mm
Weight: 1500 kg
Material: iron yoke, copper coils
Bending angle: 92.3 degrees
Central field: 1.09 T
Effective length: 0.5 m
Current: 27.2 A The device 1 further comprises intensity modulation means 7. In the example illustrated in FIGS. 1-2, the intensity modulation means 7 comprise deflecting means 13 positioned on each beam lines 8,9 downstream respectively the dipole of high momentum 11 and the dipole of low momentum 12.

The deflecting means 13 are scanning magnets, preferably fast ramping magnets or magnets capable of fast field-ramping' with the following parameters:

Size: 290 mm×205 mm×205 mm
Weight: 1500 kg
Material: iron yoke, copper coils
Duty cycle: 10%
Integrated field: 0.034 Tm
Maximal deflection angle: 100 mrad
Effective length: 0.3 m
Current: 5.6 kA;

Optionally, the intensity modulation means 6 can further comprise energy modulation means (not represented in figures). For instance, the energy modulation means to further deflect the trajectory of each train of particles bunches by an angle from 1% to 5%.

Figure 3:
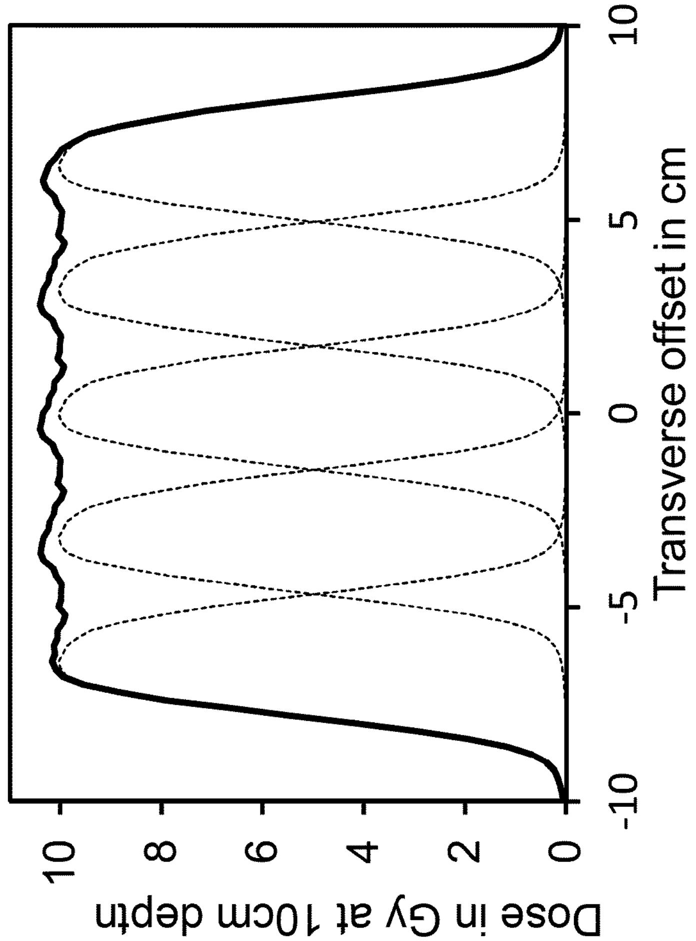
FIGS. 3 and 4 illustrate two examples of the dose distribution with intensity modulation means in the device according to the first embodiment.
Figure 4:
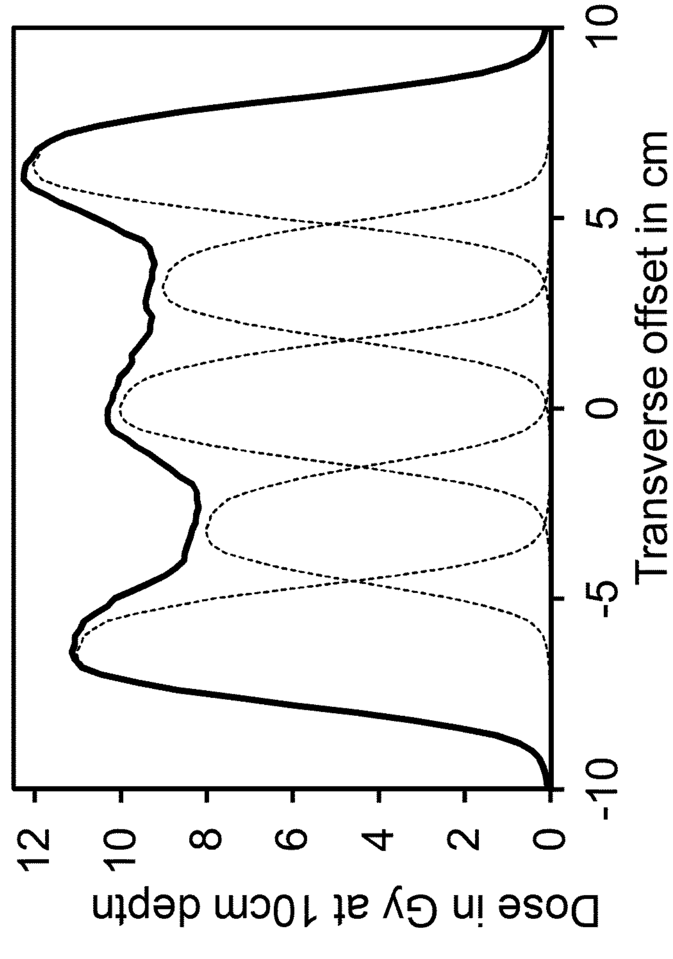

FIGS. 3 and 4 represent two examples of dose distribution that can be achieved with the present invention.

FIG. 3 shows an example of a uniform (homogeneous) dose distribution profiles of a 100 MeV beam obtained with the described intensity modulation of the present invention. FIG. 3 shows a graph of a uniform (homogeneous) dose distribution at a depth of 10 cm in a target volume produced by a single beam line. In this example, the beam has an energy of 100 MeV and the intensity modulation pattern comprises five elliptical subsections of 10 cm by 3 cm cross-section each. An average dose of 10 Gy is produced in the portions of the target volume, each portion having an area of 10×15 cm2 (in cross section) within a total time of 32 ms using 5 trains of 0.3 μs duration repeated every 8 ms. The graph shows that when 10 Gy (no modulation) is delivered to each subsection, the superposition in the transverse direction of the five adjacent subsections adds up to a uniform total dose.

FIG. 4 shows an example of a non-uniform (heterogeneous) dose distribution profiles of a 100 MeV beam obtained with the described intensity modulation of the present invention. FIG. 4 shows a graph of a non-uniform (heterogeneous) dose distribution at a depth of 10 cm in a target volume produced by a single beam line. In this example, the beam has an energy of 100 MeV and the intensity modulation pattern comprises five elliptical subsections of 10 cm by 3 cm cross-section each. An average dose of 10 Gy is produced in the portions of the target get volume, each portion having an area of 10×15 cm2 (in cross section) within a total time of 32 ms using 5 trains of 0.3 μs duration repeated every 8 ms. In contrast to FIG. 3, the graph of FIG. 4 shows that if the dose of each subsection is set to different levels—from left to right: 11 Gy, 8 Gy, 10 Gy, 9 Gy and 12 Gy—using of the modulation means of the present invention, the superposition in the transverse direction of the five adjacent subsections adds up to an intensity modulated dose distribution with a range of +/−20%. To produce other modulation patterns, the subsection charges and spot shapes will be optimized to generate the prescribed dose distribution (−140 nC, 100 nC, 120 nC, 110 nC and 150 nC for this graph).

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This for example particularly the case regarding the different apparatuses which can be used.

REFERENCE NUMBERS

1 Device according to a first embodiment
2 Electron source
3 Linear accelerator
4 Beam delivery module
5 Target volume of a patient
6 High first beam line
7 Low momentum beam line
8 Separating means
9 Intensity modulation means
10 Splitter dipole
11 Dipole of high momentum
12 Dipole of low momentum
13 Deflecting means

The invention claimed is:

1. A device for providing a radiation treatment to a patient, the device comprising:

an electron source for providing a beam of electrons, and a linear accelerator for accelerating said beam to a predetermined energy, the accelerated beam being composed of a plurality of trains of electrons bunches, and a beam delivery module for delivering the plurality of trains of electrons bunches from said linear accelerator toward the patient to treat a target volume with a radiation dose, characterized in that the device further comprises an intensity modulation means configured to modulate distribution of a radiation dose in the target volume according to a predetermined modulation pattern matching the target volume, the intensity modulation means are configured to adjust a position, a total charge and energy of each electrons bunch within a train and between trains of electrons bunches, and to separate the trains of electrons bunches depending on the total charge and/or energy of each train, the modulation pattern comprising several subsections and each subsection of said several subsections comprising trains of electron bunches with a determined charge and energy to irradiate a corresponding portion of the target volume so that the intensity modulation means allows a set radiation dose received by each portion of the target volume, the modulation pattern is determined to match the dimensions of the target volume wherein the target volume is at least about 50 $cm^3$, and/or the target volume is located at least 5 cm deep in a tissue of the patient with said radiation dose, the device being further characterized in that the radiation dose distributed by said intensity modulation means is at least 20 Gy, the radiation dose being delivered during an overall treatment time less than 50 ms.

2. The device according to claim 1, wherein the intensity modulation means are configured to further adjust an arrival angle, and projected size of each electrons bunch within a train and between trains of electrons bunches.

3. The device according to claim 1, wherein the entire radiation dose is of at least 30 Gy, or at least 35 Gy, or at least 40 Gy.

4. The device according to claim 1, wherein each portion receives a radiation dose up to an entire radiation dose.

5. The device according to claim 1, wherein each portion receives at least one train of electrons bunches.

6. The device according to claim 1, wherein the intensity modulation means comprises a charge variation means to set the charge of each train independently and direct each train to a predetermined subsection of the pattern to reach a corresponding portion of the target volume which modulates the distribution of radiation dose in the target volume.

7. The device according to claim 1, wherein the intensity modulation means comprises an energy variation means to set the energy of each train independently and direct each train to a predetermined subsection of the pattern to reach a corresponding portion of the target volume which modulates the distribution of radiation dose along the direction of the accelerated beam through the target volume.

8. The device according to claim 7, wherein each train has an energy which differs from 1% to 5%.

9. The device according to claim 1, wherein the accelerated electron beam is separated into a plurality of beam lines by a separating means, each beam lines being separated by a determined angle, and subsequently focusing each of said beam lines toward the patient to arrive in an overall time of less than 50 ms on the target volume, each beam line further comprising an independent intensity modulation means.

10. The device according to claim 9, wherein each beam line has an energy that differs from 10% to 40%.

11. The device according to claim 1, wherein the intensity modulation means comprises a deflecting means for deflecting each train of electrons bunches position transversely relative to the accelerated beam direction, said deflecting means having a deflecting speed faster than the interspacing time between two subsequent trains.

12. The device according to claim 11, wherein the deflecting means comprises a magnet.

13. The device according to claim 11, wherein the deflecting means comprises a radio frequency deflector.

14. The device according to claim 1, wherein the energy variation means is set for implementing predetermined energy variations between each train of electrons bunches, said energy variation means being operated from the linear accelerator.

15. The device according to claim 14, wherein the energy variation means is operated by controlling an amplitude and the phase of the radiofrequency pulses of the linear accelerator.

16. The device according to claim 1, wherein the intensity modulation means comprises a combination of charge variation means, energy variation means, deflection means and multiple beam lines.

17. The device according to claim 1, wherein the accelerated electron beam has a predetermined energy between 30 MeV and 250 MeV, or between 50 MeV and 250 MeV, or between 50 MeV and 150 MeV.

* * * * *